United States Patent [19]

Rivier et al.

[11] 4,444,682

[45] Apr. 24, 1984

[54] METHOD OF SULFATION

[75] Inventors: Jean E. F. Rivier, La Jolla, Calif.; Botond Penke, Budapest, Hungary

[73] Assignee: The Salk Institute for Biological Studies, San Diego, Calif.

[21] Appl. No.: 439,312

[22] Filed: Nov. 4, 1982

[51] Int. Cl.³ .................. C07C 103/52; C07C 149/20; C07C 147/02; C07C 149/40

[52] U.S. Cl. ............................. 260/112.5 R; 560/147; 560/149; 560/9; 560/11; 560/12; 560/15; 562/426; 562/429; 562/556; 564/162

[58] Field of Search ................. 260/112.5 R; 562/426, 562/429, 556; 564/162; 560/147, 149, 9, 11, 12, 15

[56] References Cited

U.S. PATENT DOCUMENTS 3,839,315 10/1974 Ondetti et al.
3,892,726 7/1975 Ondetti et al. ...................... 424/177
3,932,306 1/1976 Rona ................................ 568/896
4,102,878 7/1978 Penke et al.
4,330,466 5/1982 Yanaihara et al.

OTHER PUBLICATIONS

March, *Advanced Organic Chemistry*, 2nd Ed., McGraw-Hill Book Co., 1977, p. 333.

*Primary Examiner*—Delbert R. Phillips
*Assistant Examiner*—F. T. Moezie
*Attorney, Agent, or Firm*—Fitch, Even, Tabin & Flannery

[57] ABSTRACT

A method for sulfating a hydroxy amino acid or a residue of such an amino acid in a peptide by reaction with a reagent which is a tertiaryammonium salt of acetylsulfuric acid having the formula:

$$[CH_3COOSO_3]^-[R]^+$$

wherein R is triethylamine, ethyldiisopropylamine, pyridine, 4-methylmorpholine or 4-N,N-dimethylaminopyridine. The α-amino group and any other labile side chains present may be protected or may be left unprotected at the time the sulfation takes place.

18 Claims, No Drawings

METHOD OF SULFATION

The present invention relates to methods of sulfation of hydroxy amino acids or peptides containing residues of such acids and more particularly to such methods which achieve such sulfation without undesirable side reactions.

BACKGROUND OF THE INVENTION

The synthesis of O-sulfated hydroxy amino acids, such as tyrosine (Tyr), serine (Ser), threonine (Thr), hydroxproline (Hyp) and hydroxyleucine (Hyl), and of sulfated-amino-acid-containing peptides, e.g., cholecystokinin (CCK), caerulein (CRL), gastrin-II, has been a difficult task for peptide chemists. Although Ser and Thr could be easily sulfated or sulfatized with sulfuric or chlorosulfonic acid (A. Previero, et al., *Biochem. Biophys.* Acta 581:276, 1979), these reagents are highly reactive and cause side reactions; and during sulfation of peptides in this manner, the Tyr and Trp residue are converted into arylsulfonic acids. Another method for forming sulfate esters involves the reaction of pyridine-sulfur trioxide complex (H. C. Reitz, et al., *J. Am. Chem. Soc.* 68:1024, 1976) (British Patent No. 1,523,038) with protected hydroxy amino acids or peptides. This approach was used for the synthesis of human gastrin-II. (F. Beacham, et al., *J. Chem. Soc.* (C) 2520, 1967), of phyllocaerulein (L. Bernardi, et al., *Experientia* 25:7, 1969), of CCK - octapeptide and other CCK fragments and analogs (J. Pulscec, et al., *J. Med. Chem.* 13:349, 1970); M. Bodansky, et al., *J. Med. Chem.* 20:1047 1977), E. German Patent 128,973 (1976); D. Gillessen, et al., *Int. J. Peptide Protein Research* 13:130 1979; B. Penke, et al., *Proc. of 15th Eur. Peptide Symposium,* Wroclaw Univ. Press, Publ., Wroclaw 1979, p. 581; Hungarian Pat. No. 174500 (1976).

The most frequently used pyridine-$SO_3$ complex method has many disadvantages and leads to side reactions, such as sulfonation of tyrosine and of tryptophan, destruction of methionine and, under more drastic conditions, derivatization of guanido, thiol and amide functions on amino acid residues in the peptide. Similarly the introduction of sulfate ester group onto the tyrosine moiety of a peptide using concentrated sulfuric acid as a reagent (M. A. Ondetti, et al. *J. Am. Chem. Soc.* 92:195, 1970) is generally unsuitable for the synthesis of peptide sulfate esters because side reactions also occur, e.g., extensive sulfonation of tyrosine and tryptophan moiety, oxidation of methionine, etc. The dicyclohexylcarbodiimide (DCC)—$H_2SO_4$ method of sulfation (T. Wieland, et al., *Liebigs Ann. Chem.* 759:71, 1972) is limited to fully protected amino acids and peptides. The synthesis of N-protected tyrosine sulfate esters using a pyridine-$SO_3$ complex is another available strategy, but one which has been used for tyrosine-containing peptides only: CRL and analogs (L. Bernardi, et al., *Experientia* 28:7, 1972; L. Moroder, et al., Hoppe Seyler's *Z. Physiol. Chem.,* 360:787, 1979), of CCK-octapeptide (B. Penke, et al., Proc. 16th *Eur. Peptide Symp.*) Accordingly, investigators continued to seek new methods of sulfation which do not have the aforementioned disadvantages of the occurrence of potential side reactions.

SUMMARY OF THE INVENTION

A general method has been found which is suitable for the synthesis of sulfate esters of hydroxy amino acids or residues thereof within a peptide or within a peptide hydrazide sequence without side reaction of the above-mentioned side chains. This method sulfates substantially only the unprotected hydroxyl group while other labile groups are unprotected or protected as desired.

Briefly, the invention provides a method for sulfating a hydroxy amino acid or a residue of such an amino acid in a peptide by reaction with a reagent which is a tertiaryammonium salt of acetylsulfuric acid having the formula:

$$[CH_3COOSO_3]^-[R]^+ \qquad \text{Reagent I}$$

wherein R is triethylamine, ethyldiisopropylamine, pyridine, 4-methylmorpholine or 4-N,N-dimethylaminopyridine.

We have found a general method suitable for synthesis of sulfate esters of hydroxy amino acids as such, or within a peptide or a peptide hydrazide sequence, without any substantial side reactions while other labile side-chain groups are protected and unprotected. The reaction is preferably carried out at room temperature and atmospheric pressure by allowing the reactants to stand for about 2–5 days in an appropriate mutual solvent. Other equivalent reaction conditions may be used.

These new reagents can be easily synthesized by reacting a mixture of acetic anhydride and an appropriate tertiary amine, e.g., triethylamine, diisopropylethylamine, N-methylmorpholine, pyridine, 4-N,N-dimethylaminopyridine, etc., with sulfuric acid at 0° C. The tertiaryammonium salts of acetylsulfuric acid are stable, crystalline compounds which react only with the alcoholic or the phenolic hydroxyl group of hydroxyamino acids (e.g. serine, threonine, hydroxyproline, hydroxyleucine and tyrosine) and which do not readily react with free amino, guanido, imidazole, hydrazide, sulfhydryl or thioether groups present either in free amino acids or in side chains in peptides.

The reaction can be carried out with other labile side-chain groups either protected or unprotected in amino acids and peptides, and the unprotected hydroxyl group may be anywhere in the chain, i.e., it may be at either end of a peptide or a peptide fragment may be at both ends. The $\alpha$-amino group of the free amino acid or the N-terminus of the peptide may be unprotected, acylated or protected by tert-butyloxycarbonyl (BOC), fluorenylmethyloxy-carbonyl (FMOC) or benzyloxycarbonyl (Z). If acylated, the acyl group would generally not have more than about 12 carbon atoms. Likewise, the C-terminus of the amino acid, or of a peptide or a peptide fragment located there, may have substantially any of the usual groups attached thereto, such as OH, OMe, OEt, OBzl, $NH_2$ and $N_2H_3$. They may also have other groups useful in active-ester coupling, such as —$OC_6H_4NO_2$ (p. nitrophenoxy),
—$OC_6F_5$ (pentafluorophenoxy),
—$OC_6Cl_5$ (pentachlorophenoxy) and

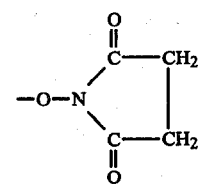

The sulfation reaction may also be carried out while the peptide is attached to a resin upon which it is being formed by solid-phase synthesis.

Peptides are compounds which contain two or more amino acids in which the carboxyl group of one acid is linked to the amino group of the other acid. The formula for a peptide is represented in accordance with conventional representation of peptides where the amino group appears to the left and the carboxyl group to the right. The position of the amino acid residue is identified by numbering the amino acid residues from left to right. In the case of GnRH, for example, the hydroxyl portion of the carboxyl group of glycine has been replaced with an amino group ($NH_2$) and is so indicated; if there is no indication, it should be assumed the OH group is present. Likewise, if there is no indication at the N-terminus, the α-amino group is unsubstituted. The abbreviations for the individual amino acid residues above are conventional and are based on the trivial name of the amino acid, e.g., p-Glu is pyroglutamic acid, His is histidine, Trp is tryptophan, Gly is glycine, Leu is Leucine, Arg is arginine, Pro is proline, Phe is phenylalanine and Ala is alanine. Except for glycine, amino acids of the peptides described hereinafter are of the L-configuration; however D-isomer amino acids could be used if desired.

The main advantages of the application of acetyl sulfuric acid tertiary ammonium salts for sulfation of amino acids and peptides are the following: easy synthesis of the reagents and selective reaction with the hydroxyl groups without significant side reactions, hence high yields and high purity of sulfate esters synthesized. For example, for the synthesis of free hydroxyamino acid sulfate esters, the appropriate amino acid (Ser, Thr or Tyr) is dissolved in a mixture of dimethylformamide-pyridine 1:1 (v/v), and a 3-fold excess of Reagent I (e.g., acetylsulfuric acid pyridinium salt) is added. Upon standing for two days at 20° C., the reaction mixture is neutralized with sodium hydroxide dissolved in methanol, and the hydroxyamino acid sulfate ester sodium salt is precipitated by addition of ether (e.g., diethylether) to the solution. Similarly, N-protected (BOC,FMOC, etc.) amino acids may be dissolved in dry pyridine, at 20° C., and 1.5-fold excess of acetylsulfuric acid pyridinium salt is added and left to react overnight. The pyridine is evaporated, and the oily residue is dissolved in water and the pH adjusted to 8.0 with sodium or potassium hydroxide. The pyridine which is liberated is removed by ether extraction. The pH is adjusted to 3.5 with dilute $H_2SO_4$, and the aqueous solution is lyophilized. The N-protected amino acid sulfate ester monosodium or monopotassium salts are soluble in dichloromethane while the other salts ($Na_2SO_4$, $K_2SO_4$) are eliminated by filtration. The final product is obtained after addition of ether to the $CH_2Cl_2$ solution. The N-protected amino acid sulfate ester alkali salts are stable, crystalline compounds and may be directly employed in liquid-phase or solid-phase peptide syntheses.

In general, sulfate-ester-containing peptides are prepared by either: (a) introducing the sulfate ester group(s), using the acetylsulfuric acid Reagent I, directly into a synthetic peptide containing a hydroxyamino acid residue; or (b) introducing the appropriate N-protected hydroxyamino acid sulfate ester into the peptide chain during the stepwise synthesis of the peptide.

An automatic peptide synthesizer (Beckman, Model 990B) is used for the solid-phase synthesis of peptides. The standard cycle of coupling, acetylation of uncoupled amino groups and deblocking is as follows:

| STEP | REAGENTS AND OPERATIONS | MIX TIMES MIN. |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2CL_2$-70 ml. (2 times) | 10 |
| 5 | $CH_2Cl_2$ wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

The HF cleavage of the peptides from the resin and deprotection is performed in nonaqueous medium at 0° C. for 45 minutes. Peptide purity control is checked by reverse phase HPLC. The preparative HPLC purification is achieved on Waters Associates Prep LC500 using custom-made cartridges. Optical rotations are measured on a Perkin-Elmer spectropolarimeter. Peptide hydrolysis is performed in 4M methane sulfonic acid containing 0.2% tryptamine, using hydrolysis time of 24 hours at 110° C. in sealed ampules under high vacuum. For amino acid analysis, the hydrolysates are neutralized and loaded to the column of Beckman automatic amino acid analyzer model 121M. Melting points are not corrected.

The following Examples are exemplary of the formation of the reagents and their reactions with amino acids and with peptides:

EXAMPLE I

Acetylsulfuric acid pyridinium salt

A mixture of 30 ml of acetic anhydride and 8.05 ml (0.1 mole) of pyridine is cooled to 0° C., and 5.4 ml of conc. $H_2SO_4$ is added dropwise at 0° C. under stirring. After 10 minutes, the crystals are filtered, washed with diethyl ether and dried under vacuum over $P_2O_5$ and KOH. Yield: 18.4 g (84%). IR: 1050 $cm^{-1}$ sharp band, characteristic for sulfates and sulfate esters. Decomposes above 60° C., very hygroscopic. MW: 219.2 ($C_7H_9O_5NS$).

EXAMPLE II

Acetylsulfuric acid, p. dimethylamino pyridinium salt

A mixture of 15 ml acetic anhydride and 6.1 g (0.05 moles) of p. dimethylamino pyridine is stirred at 0° C., and 2.7 ml (0.05 moles) of conc. $H_2SO_4$ is added in 2 minutes. The reagent precipitates after 3 minutes as colorless crystals. After adding 200 ml of ether, the crystals are filtered, washed with ether and dried under vacuum. Yield: 10.6 g (81%), hygroscopic yellow crystals. IR: 1050 $cm^{-1}$, sharp band. Decomposes above 75° C. MW: 262.3 ($C_9H_{14}O_5N_2S$).

EXAMPLE III

Tert. butyloxycarbonyl serine sulfate ester sodium salt 10.25 g (0.05 moles) of Boc-Ser is dissolved in 100 ml of pyridine, and 16.5 g (75 moles) of acetylsulfuric acid pyridinium salt is added under stirring. After standing overnight at 20° C., the clear solution is evaporated to dryness. The oily residue is dissolved in 300 ml of water, and the pH is adjusted with 1N NaOH to 8.0. The liberated pyridine is extracted 3 times with diethyl ether. The pH of the aqueous solution is readjusted with 1N $H_2SO_4$ to 3.5 and lyophilized. To the fluffy white powder, 100 ml of $CH_2Cl_2$ is added; the insoluble material ($Na_2SO_4$) is centrifuged and discarded. 200 ml of ether is added to the dichloromethane solution, and the material precipitates as white crystals. After filtering, Boc-Ser($OSO_3Na$) is washed with ether and dried under vacuum. Yield: 13 g (84%); MW: 309.3; IR: sharp band at 1050 cm$^{-1}$. $[\alpha]_D^{20} = +3.2°$ (c=1,$H_2O$).

The Boc-D-Ser sulfate ester sodium salt is also synthesized under the same conditions. 4.1 g. (0.02 moles) of Boc-Ser, yields 4.63 g (75%) of end product. $[\alpha]_D^{20} = -3.2°$(c=1,$H_2O$).

The reaction is repeated using acetylsulfuric acid methylmorpholinium salt as the reagent, and the resulting sulfate ester sodium salt is the same in all respects.

EXAMPLE IV

Tert. butyloxycarbonyl-threonine sulfate ester, sodium salt

Boc-Thr($OSO_3Na$) is synthesized from 10.9 g (0.05 moles) of Thr, using the general procedure described in Example III and yielding 14.5 g (89.7%) of Boc-Thr sulfate ester sodium salt. MW: 323.3; $[\alpha]_D^{20} = -13.2°$(c=1,$H_2O$); IR:sharp band at 1050 cm$^{-1}$.

EXAMPLE V

Tert. butyloxycarbonyl 3-hydroxyproline sulfate ester, sodium salt

Boc-Hyp($OSO_3Na$) is synthesized from 10.0 g. (0.043 moles) of Boc-3-Hyp and 14.3 g (0.065 moles) of acetylsulfuric acid pyridinium salt as generally described in Example III. Yield: 13 g (82%);IR: sharp band at 1080 cm$^{-1}$.

The reaction is repeated using acetylsulfuric acid methylmorpholinium salt as the reagent, and the resulting sulfate ester sodium salt is the same in all respects.

EXAMPLE VI

Tert. butyloxycarbonyl-tyrosine sulfate ester, sodium salt

Boc-Tyr($OSO_3Na$) is synthesized from 11.24 g. (0.04 moles) of Boc-Tyr and 13.2 g (0.06 moles) of acetylsulfuric acid pyridinium salt as generally described in Example III. Yield: 14.2 g (92.6%) MW: 383.5; $[\alpha]_D^{20} = +4.7°$(c=1,$H_2O$); IR: sharp band at 1080 cm$^{-1}$.

EXAMPLE VII

Cholecystokinin octapeptide sulfate ester

CCK-8, Asp-Tyr($OSO_3H$)-Met-Gly-Trp-Met-Asp-Phe-$NH_2$ is prepared by solid-phase synthesis as follows: FMOC-Asp-Tyr-Met-Gyl-Trp-Met-Asp-Phe-$NH_2$ is built up in a stepwise manner using a methylbenzhydrylamino (MBHA) resin as polymer support; using BOC-protected amino acids and using DCC as the coupling reagent. The phenol hydroxyl of Tyr is protected with the 2,6-dichlorobenzyl group during the peptide synthesis.

Boc-Phe (1.59 g: 6 mmoles) is coupled onto an MBHA resin (6.0 g: 2.4 mmoles) at a free amino group on the resin. The following 7 residues are sequentially attached thereafter using the standard synthesis scheme shown in Table I: Boc-Asp(OBzl) 1.94 g (6 mmoles); Boc-Met 1.5 g (6 mmoles); Boc-Trp 1.83 g (6 mmoles); Boc-Gly 1.05 g (6 mmoles); Boc-Met 1.5 g (6 mmoles); Boc-Tyr(2,6 dichloro Bzl) 2.64 g (6 mmoles); and FMOC-Asp (0-But) 2.46 g (6 mmoles). Each of the amino acids is dissolved in 45 ml of $CH_2Cl_2$, except for Boc-Trp and FMOC-Asp(OBut) which are dissolved in $CH_2Cl_2$ containing 10% DMF. 6 mmoles of dicyclohexylcarbodiimide (DDC) dissolved in $CH_2Cl_2$ is used for each coupling.

After the last coupling step, the octapeptidyl-resin is dried in vacuo, and the FMOC-CCK-octapeptide is cleaved from the polymer support with HF(90 ml), 10 ml of anisole and 1ml of methylethyl-sulfide(MES) at 0° C., which also removes the side-chain protecting groups. The Nα-protected octapeptide is dissolved in 50 ml of DMF and filtered to eliminate the resin. It is then precipitated with 50 ml of ethyl ether, yielding 2.0 g. of a white solid material.

After drying, it is dissolved in DMF (10 ml) and pyridine (8 ml) to which acetylsulfuric acid pyridinium salt 1.5 g (7 mmoles) is added. After standing for 3 days at 20° C., 2 ml (20 mmoles) of piperidine is added to cleave the N-terminus fluorenylmethyloxycarbonyl group. The reaction mixture is left for 30 minutes at room temperature, then neutralized with 1.2 ml (20 mmoles) of acetic acid and evaporated to dryness. The resulting yellow oil is triturated with 30 ml 0.1N HCl at 0° C., and the peptide which precipitates as a white solid is isolated by centrifugation. The CCK-octapeptide sulfate ester obtained is dissolved in 30 ml $CH_3OH$ and 470 ml of $H_2O$, and pH is adjusted to about 6.5 using NaOH. The insoluble colloidal material is filtered off on cellite, and the peptide is purified by preparative reverse phase HPLC using a gradient of acetonitrile in 0.1M $NH_4$-acetate (pH=6.5). 555 mg (0.44 mmoles) of cholecystokinin octapeptide sodium salt (Asp-Tyr-($OSO_3Na$)-Met-Gly-Trp-Met-Asp-Phe-$NH_2$) is isolated from the aqueous solution after two lyophilizations. Amino acid analysis is consistent with expected values, and a single peak is shown on HPLC. IR: sharp band at 2050 cm$^{-1}$;$[\alpha]_D^{20} = -22.4°$(c=2,DMF).

The synthesis is repeated using acetylsulfuric acid triethylamine salt as the reagent, and the resulting peptide is comparable in all respects.

EXAMPLE VIII

Hexagastrin sulfate ester (Tyr($OSO_3Na$)-Gly-Trp-Met-Asp-Phe-$NH_2$)

Hexagastrin (Tyr-Gly-Trp-Met-Asp-Phe-$NH_2$) is synthesized on 6.0 g (1.4 mmoles) of MBHA resin as generally described in Example VII. The protected amino acids that are used are: Boc-Phe (1.59 g, 6 mmoles); Boc-Asp(OBzl) (1.94 g, 6 mmoles); Boc-Met (1.5 g, 6 mmoles); Boc-Trp (1.83 g, 6 mmoles); Boc-Gly (1.05 g, 6 mmoles) and Boc-Tyr (2,6-dicloro Bzl) (2.64 g, 6 mmoles). The hexapeptide is cleaved from the resin and all protecting groups are removed using 90 ml of HF, 10 ml of anisole and 1 ml MES for 45 minutes at 0° C., dissolved in acetic acid and filtered to eliminate the resin. The solution is diluted with water and lyophilized, yielding 1.0 g of hexagastrin. 350 mg of this peptide is dissolved in 4 ml of DMF and 2 ml of pyridine, and 400 mg (1.8 mmoles) of acetylsulfuric acid pyridinium salt is added. The solution is left for 4 days at room temperature. Finally, 400 ml of water is added to the reaction mixture, and the pH of the solution is adjusted to 7.2 with 1N NaOH. The hexagastrin sulfate ester is purified on reverse phase HPLC, and 90 mg of hexagastrin sulfate ester sodium salt is obtained after two lyophilizations. Amino acid analysis gives the expected ratios. IR: sharp band at 1080 cm$^{-1}$. $[\alpha]_D^{20} = -11.5°(C=1, H_2O)$.

The synthesis is repeated using acetylsulfuric acid triethylamine salt as the reagent, and the resulting peptide is comparable in all respects.

EXAMPLE IX

Caerulein and [Thr(Ac)$^5$]-caerulein sulfate esters (pGlu-Gln-Asp-Tyr(OSO$_3$Na)-Thr-Gly-Trp-Met-Asp-Phe-NH$_2$ and
pGlu-Gln-Asp-Tyr(OSO$_3$Na)-Thr(Ac)-Gly-Trp-Met-Asp-Phe-NH$_2$)

The protected caerulein (CRL) decapeptide is synthesized as described in Example VII on 5.0 g MBHA resin (1.15 mmoles). The protected amino acids used are: Boc-Phe (1.32 g, 5 mmoles); Boc-Asp(OBzl) 1.62 g, 5 mmoles); Boc-Met (1.25 g, 5 mmoles); Boc-Trp (1.52 g, 5 mmoles); Boc-Gly (0.88 g, 5 mmoles); Boc-Thr(Ac) (1.3 g. 5 mmoles); Boc-Tyr(2,6-dichloro Bzl) (2.2 g, 5 mmoles); Boc-Asp(OBzl) (1.62 g, 5 mmoles); Boc-Gln(Xan) (2.13 g, 5 mmoles); Z-pGlu (1.32 g, 5 mmoles). The decapeptide is cleaved from the resin and all protecting groups are removed with a mixture of 90 ml HF, 10 ml anisole and 1 ml MES; it is washed thoroughly with ethyl ether and dissolved in 40 ml of DMF before filtration. Precipitation with 500 ml of ethyl ether gives 1.1 g of the non-sulfated CRL decapeptide pGlu-Gln-Asp-Tyr-Thr(AC)-Gly-Trp-Met-Asp-Phe-NH$_2$ as a white powder. 1.0 g (0.91 mmoles) of this material is dissolved in 10 ml of DMF and 5 ml of pyridine to which 1.0 g (4.55 mmoles) of acetylsulfuric acid pyridinium salt is added. After standing 4 days at 20° C., 500 ml of water is added to the reaction mixture, and the pH is adjusted to 7.00 with 4N NaOH. The decapeptide sulfate ester is then purified by preparative reverse phase HPLC, applying a gradient of CH$_3$CN in 0.1M NH$_4$-acetate buffer. 350 mg of pure [Thr(Ac)$^5$]-caerulein, i.e. pGlu-Gln-Asp-Tyr(OSO$_3$Na)-Thr(Ac)-Gly-Trp-Met-Asp-Phe-NH$_2$, is isolated after 2 lyophilizations of the collected fractions. Amino acid analysis is consistent with the expected values; IR: sharp band at 1080 cm$^{-1}$; $[\alpha]_D^{20} = -26.5°(c=1, H_2O, pH 8.0)$.

In order to hydrolyze the acetyl group of the Thr residue, 18 mg of pure [Thr(Ac)$^5$]-CRL is dissolved in 600 μl of H$_2$O, and 75 μl of 1M NaOH is added (pH 12.0) and left to react at 20° C. under a nitrogen atmosphere. After 20 minutes, the solution is neutralized by addition of 2.4 ml of 0.1M NH$_4$ acetate buffer (pH=6.5). Purification of caerulein (sulfate ester) is achieved on a semi-preparative reverse phase HPLC column applying a gradient of CH$_3$CN in 0.1 M NH$_4$-acetate buffer (pH=6.5), yielding 8.0 mg of pure caerulein after two lyophilizations. Amino acid analysis is consistent with expected values; IR: sharp band at 1080 cm$^{-1}$; $[\alpha]_D^{20} = -26.8°(c=1, H_2O, pH 8.0)$.

EXAMPLE X

[Ser(OSO$_3$Na)$^4$]-LRF (pGlu-His-Trp-Ser(OSO$_3$Na)-Try-Gly-Leu-Arg-Pro-Gly-NH$_2$)

Because the alcoholic hydroxyl group reacts faster with Reagent I than does the phenolic hydroxyl of Tyr, it is possible to synthesize Tyr-containing peptides with Ser-sulfate ester, Thr-sulfate ester and Hyp-sulfate ester only. [Ser(OSO$_3$H)$^4$]-LRF having the formula pGlu-His-Trp-Ser(OSO$_3$H)-Tyr-Gly-Leu-Arg-Pro Gly-NH$_2$ is prepared as follows: 130 mg of LRF decapeptide, also referred to as LH-RH and GnRH, is dissolved in DMF-pyridine 3:2 (v/v), and a 6-fold excess of acetylsulfuric acid pyridinium salt (132 mg) is added. After 4 hours standing at 20° C., the reaction mixture is diluted with water, and pH is adjusted to 7.2 with 1N NaOH. The Ser-sulfate ester analog of LRF is isolated on preparative HPLC-column using an acetonitrile gradient in triethylammonium phosphate buffer, pH=2.25. Under these conditions a negligible amount of Tyr hydroxyl reacts with Reagent I, and the Ser-sulphate ester analog of LRF is isolated in about a 50% yield. $[\alpha]_D^{20} = -42°(c=0.5, 50\% H_2O/CH_3OH)$.

The synthesis is repeated using acetylsulfuric acid ethyldiisopropylamine salt as the reagent, and the resulting peptide is comparable in all respects.

EXAMPLE XI

[Ser(OSO$_3$Na)$^4$]-LRF (pGlu-His-Trp-Ser(OSO$_3$Na)-Tyr-Gly-Leu-Arg-Pro-Gly-NH$_2$)

The N-protected hydroxyamino acid sulfate esters can be applied directly in the stepwise build-up of peptides.

The decapeptide is synthesized on 3.0 g (1.1 mmole) benzhydrylamino resin using the general process described earlier in Example VII. Introduction of the Ser-sulfate ester moiety into the molecule is accomplished using BOC-Ser sulfate ester sodium salt.

The following protected amino acids are used: Boc-Gly (0.53 g, 3 mmoles); Boc-Pro (0.65 g, 3 mmoles); Boc-Arg(Tos)(1.28 g, 3 mmoles); Boc-Leu (0.75 g, 3 mmoles); Boc-Gly (0.53 g, 3 mmoles); Boc-Tyr(2,6-dichloro Bzl) (1.32 g, 3 mmoles); Boc-Ser (OSO$_3$Na) (3.1 g, 10 mmoles); Boc-Trp (0.92 g, 3 mmoles); Boc-His(Tos) (1.23 g, 3 mmoles); Z-pGlu (0.80 g, 3 mmoles). All couplings are mediated by DCC. Boc-Ser(OSO$_3$Na) (10 mmoles) is coupled in the presence of 11 mmoles (2.1 g) of pentafluorophenol in 30 ml CH$_2$Cl$_2$. The peptide is cleaved from the resin and deprotected with 50 ml of HF containing 5 ml of anisole (40 minutes at 0° C.). The crude decapeptide (1.0 g) is dissolved in 500 ml of H$_2$O, and the pH is adjusted to 7.0 with NaOH. The peptide is purified by reverse phase HPLC using a gradient of CH$_3$CN in triethylammonium phosphate buffer, pH 2.25 and desalting using 0.1% TFA/CH$_3$CN on preparative HPLC. 232 mg of pure [Ser(OSO$_3$Na)$^4$]-LRF is isolated after 2 lyophilizations. Amino acid analysis is consistent with expected values. $[\alpha]_D^{20} = -41.2°(C=0.5, 50\% H_2O/CH_3OH)$.

There are some differences between acid stability of the sulfate esters of various amino acids. Under basic conditions, all the sulfate esters are stable, but under acidic conditions, the sulfate ester of Tyr cleaves easily as set forth in Table II.

TABLE II

Stability of sulfate esters of various hydroxy amino acids under basic and acidic conditions.

| Amino Acid Sulfate Ester | 0.01N NaOH 20° C. | 2N NaOH 110° C. | 100% TFA | 50% TFA in $CH_2Cl_2$ | HF 0° C. |
|---|---|---|---|---|---|
| $Tyr(OSO_3H)$ | S | U | X(60 min) | S(60 min) | U(45 min) |
| $Ser(OSO_3H)$ | S | U | S(2 days) | S(2 days) | X(45 min) |
| $Thr(OSO_3H)$ | S | U | S(2 days) | S(2 days) | X(45 min) |
| $Hyp(OSO_3H)$ | S | U | S(2 days) | S(2 days) | X(45 min) |

Abbreviations:
S = Stable, no cleavage
U = Unstable
X = 20-30% cleavage

The conclusion from the stability data in Table II is that all peptides and peptide amides containing the sulfate esters of Ser, Thr and/or Hyp can be formed by solid-phase synthesis with application of HF cleavage of the peptide sulfate ester from the polymer support. Tyr-sulfate-ester-containing peptides cannot be synthesized in this manner due to their higher acid lability; however, it is possible to build up Tyr-sulfate-ester-containing peptides on a solid-phase resin and cleave them from the polymer support with hydrazine as protected peptide hydrazides. Such compounds are suitable for fragment condensation as precursors of larger peptides.

EXAMPLE XII

The protected N-terminal pentapeptide sulfate ester hydrazide of LRF, i.e. pGlu-His-Trp-Ser(Bzl)-Tyr-$(OSO_3Na)$—$N_2H_3$, is synthesized by reacting BOC-Tyr sulfate ester sodium salt with chloromethylated polystyrene in DMF in the presence of KF. The BOC group is cleaved with 50% TFA acid in $CH_2Cl_2$, and the peptide is built up stepwise on the polymer support using BOC-protected amino acids and DCC as coupling agent. The amino acids used are: Boc-Ser(Bzl) (1.8 g, 6 mmoles); Boc-Trp (1.82 g, 6 mmoles); Boc-His(Tos) (2.46 g, 6 mmoles); pGlu (0.78 g, 6 mmoles). After completion of the synthesis, the resin is suspended in 30 ml of DMF, and 1.35 ml (42 moles) of dry hydrazine is added. After 15 hours, the hydrazine is neutralized with acetic acid 4.84 ml (84 mmoles). The resin is filtered and discarded, and the pentapeptide sulfate ester hydrazide is precipitated with the addition of diethyl ether, 600 ml, to the DMF solution. The peptide is further purified by precipitation from a methanolic solution (30 ml) with ether (500 ml), filtered, washed with water and dried. Yield: about 900 mg of protected pentapeptide sulfate ester hydrazide. Amino acid analysis is consistent with expected values. $[\alpha]_D^{20} = +9.7°$ (C=1, DMF). IR: sharp band at 1080 cm$^{-1}$.

The synthesis is repeated using acetylsulfuric acid triethylamine salt as the reagent, and the resulting peptide is comparable in all respects.

EXAMPLE XIII

N-terminal tetrapeptide sulfate ester hydrazide of CRL pGlu-Gln-Asp-Tyr$(OSO_3Na)$-$N_2H_3$ is synthesized in a similar way to Example XII. Asp is protected with tert. butyl ester and coupled with DCC to the Tyr-sulfate ester-resin. After deblocking with 50% TFA/$CH_2Cl_2$(v/v), BOC-Glu(p-nitrophenyl ester) and pGlu(pentafluorophenyl ester) are respectively used for stepwise coupling. The tetrapeptide sulfate ester is cleaved from the resin in DMF with 30-fold excess hydrazine and isolated by precipitation with ethyl ether. It is further purified by precipitation from DMF with ethylacetate, yielding a pure Caerulein 1-4 tetrapeptide hydrazide suitable for further synthesis.

The synthesis is repeated using acetylsulfuric acid triethylamine salt as the reagent, and the resulting peptide is comparable in all respects.

EXAMPLE XIV

As mentioned above, amino acids containing alcoholic hydroxyl groups react faster with Reagent I than does the phenolic hydroxyl of Tyr. This allows for the selective sulfation of the Ser$^4$-residue in LRF. Longer reaction time will lead to sulfation of some Tyr too. Two analogs of cholecystokinin, i.e., [Ser$(OSO_3Na)_2$.$^7$]acetyl-CCK (2-8), and [Tyr$(OSO_3Na)^2$,Ser$(OSO_3Na)^7$]acetyl-CCK(2-8), are synthesized as follows: The acetyl heptapeptide Ac-Tyr-Met-Gly-Trp-Met-Ser-Phe is assembled on an MBHA resin using BOC for N-protection. Tyr is protected with 2,6 dichlorobenzyl ether and Ser with Bzl. Acetylation of the heptapeptide is performed on the resin by reacting the heptapeptidyl-resin with acetic anhydride in $CH_2Cl_2$. After HF-cleavage and deprotection (in the presence of 10% anisole and 1% MES as scavengers) to produce the acetyl heptapeptide amide, it is purified by precipitation from DMF with ethyl ether and dissolved in DMF-pyridine 2:1 (v/v). A 5-fold excess of acetylsulfuric acid pyridinium salt is then added. After standing for 5 days at 20° C., the reaction mixture is diluted with water, and the pH of the solution is adjusted to 7.5 with NaOH. The two peptides, Ac-Tyr$(OSO_3Na)$-Met-Gly-Trp-Met-Ser$(OSO_3Na)$-Phe-$NH_2$ and Ac-Tyr-Met-Gly-Trp-Met-Ser$(OSO_3Na)$-Phe-$NH_2$, in a ratio of about 1:1, separate on a reverse phase preparative HPLC column. The more hydrophilic disulfate ester has a shorter retention time and is easily separated from the less hydrophylic monosulfate ester and from the unreacted starting material.

Analogs of the Ac-CCK-(2-8) heptapeptide containing sulfate ester of Thr in the 7-position instead of Ser are synthesized in the same way to obtain

[Thr$(OSO_3Na)^7$] Ac-CCK-(2-8) and
[Tyr$(OSO_3Na)^2$,Thr$(OSO_3Na)^7$] Ac-CCK-(2-8) in a ratio of about 1:1. A similar ratio is obtained for the appropriate analogs of Ac-CCK-(2-8) when Hyp is substituted in the 7-position.

As a conclusion, a new class of reagents (acetylsulfuric acid tertiary ammonium salts) has been found which will sulfate the free hydroxyl groups of free and protected amino acids or peptides under very mild conditions and without significant side reactions. The invention provides an easy and rational solid-phase-synthesis strategy for obtaining large quantities of peptide sulfate esters of high biological importance, such as cholecystokinin, caerulein, etc.

The sulfate ester products synthesized with Reagent I may be characterized by the following general formulas II and III:

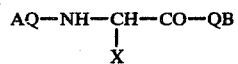

II wherein A=H,acyl, Boc, FMOC or Z;
wherein Q=one or more amino acids joined in peptide linkage to one another or des-Q;
wherein X=$CH_2$—$OSO_3H$, $CH(CH_3)$—$OSO_3H$, $CH(OSO_3H)CH(CH_3)_2$ or

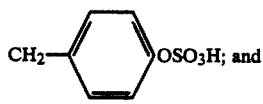

wherein B=OH, OMe, OEt, OBzl, NH₂, N₂H₃, NH[resin support], O—CH₂—[resin support], or —OC₆H₄NO₂, —OC₆F₅, —OC₆Cl₅ or

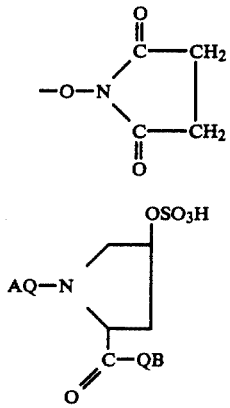

III wherein A, B and Q are defined as above.

Although the invention has been described with regard to its preferred embodiments, it should be understood that changes and modifications as would be obvious to one having the ordinary skill in this art may be made without departing from the scope of the invention which is set forth in the claims which are appended hereto. For example, any of the naturally occurring L- or D-isomer amino acids may be used in the peptides that are formed in accordance with the invention, and there is no reason that unnatural amino acids cannot also be used.

Particular features of the invention are emphasized in the claims that follow.

What is claimed is:

1. A method for sulfating a hydroxy amino acid or a residue of such an amino acid in a peptide, which method comprises reacting the amino acid or the peptide with a reagent which is a tertiaryammonium salt of acetylsulfuric acid having the formula

[CH₃COOSO₃]⁻[R]⁺ wherein R is triethylamine, ethyldiisopropylamine, pyridine, 4-methylmorpholine or 4-N,N-dimethylaminopyridine.

2. A method in accordance with claim 1 wherein R is pyridine.

3. A method in accordance with claim 2 wherein said reaction takes place with a peptide containing a first amino acid residue having an unprotected hydroxy group and a second amino acid residue having an unprotected side chain.

4. A method in accordance with claim 1 wherein said reaction takes place with a peptide containing first and second amino acid residues each having an unprotected hydroxy group.

5. A method in accordance with claim 4 wherein said first residue is Ser, Thr, Hyp or Hyl and said second residue is Tyr and wherein the conditions are such that a substantial portion of said Tyr residue is not sulfated during the reaction.

6. A method in accordance with claim 2 wherein cholecystokinin or an analog thereof or a fragment of either is the peptide that is reacted.

7. A method in accordance with claim 2 wherein caerulein or an analog thereof or a fragment of either is the peptide that is reacted.

8. A method in accordance with claim 2 wherein LRF or an analog thereof or a fragment of either is the peptide that is reacted.

9. A method in accordance with claim 2 wherein a fragment of gastrin or an analog thereof is the peptide that is reacted.

10. A method in accordance with claim 1 wherein R is 4-N,N-dimethylamino pyridine.

11. A method in accordance with claim 1 wherein R is triethylamine.

12. A method in accordance with claim 1 wherein R is ethyldiisopropyl amine.

13. A method in accordance with claim 1 wherein said reaction takes place with a peptide containing a first amino acid residue having an unprotected hydroxy group and a second amino acid residue having an unprotected side chain.

14. A method in accordance with claim 1 wherein said reaction takes place with a peptide containing first and second amino acid residues each having an unprotected hydroxy group.

15. A method in accordance with claim 14 wherein said first residue is Ser, Thr, Hyp or Hyl and said second residue is Tyr and wherein the conditions are such that a substantial portion of said Tyr residue is not sulfated during the reaction.

16. A method in accordance with claim 1 wherein cholecystokinin or an analog thereof or a fragment of either is the peptide that is reacted.

17. A method in accordance with claim 1 wherein caerulein or an analog thereof or a fragment of either is the peptide that is reacted.

18. A method in accordance with claim 1 wherein LRF or analog thereof or a fragment of either is the peptide that is reacted.

* * * * *

UNITED STATES PATENT AND TRADEMARK OFFICE
CERTIFICATE OF CORRECTION

PATENT NO. : 4,444,682

DATED : April 24, 1984

INVENTOR(S) : Jean E. F. Rivier et al.

It is certified that error appears in the above-identified patent and that said Letters Patent is hereby corrected as shown below:

Column 1, line 4, as an initial paragraph, insert:
--This invention was made with Government support under Grant No. AM-26741 awarded by the National Institutes of Health. The Government has certain rights in this invention--.

Column 1, line 32, correct the spelling of "Bodanszky".

Column 1, line 43, after "Similarly" insert a comma (,).

Column 2, line 31, change "tertiaryammonium" to --tertiary ammonium--.

Column 3, line 42, change "(BOC,FMOC, etc.)" to --(BOC, FMOC, etc.)--.

Column 4, line 12, change "$CH_2CL_2$" to --$CH_2Cl_2$--.

Column 4, line 68, change "$(C_9H_{14}O5N_2S)$" to --$(C_9H_{14}O_5N_2S)$--.

Column 5, lines 16-17, change "Boc-Ser($OSO_3Na$)" to --Boc-Ser($OSO_3Na$)--.

Column 7, line 51, after "i.e." insert a comma (,).

UNITED STATES PATENT AND TRADEMARK OFFICE
CERTIFICATE OF CORRECTION

PATENT NO. : 4,444,682

DATED : April 24, 1984

INVENTOR(S) : Jean E. F. Rivier et al.

It is certified that error appears in the above-identified patent and that said Letters Patent is hereby corrected as shown below:

Column 9, line 31, after "i.e." insert a comma (,).

Column 9, delete lines 54-56.

Column 10, delete lines 4-6.

Column 12, line 6, change "1" to --2--.

Signed and Sealed this

Twentieth Day of November 1984

[SEAL]

Attest:

GERALD J. MOSSINGHOFF

Attesting Officer

Commissioner of Patents and Trademarks